US012714408B2

(12) United States Patent
Deppmeier et al.

(10) Patent No.: US 12,714,408 B2

(45) Date of Patent: Aug. 25, 2026

(54) INSERTION TOOL

(71) Applicant: Platform Innovations, Inc., Naples, FL (US)

(72) Inventors: Thomas Deppmeier, Santa Ynez, CA (US); Steven Jones, Naples, FL (US)

(73) Assignee: Platform Innovations, Inc., Naples, FL (US)

( * ) Notice: Subject to any disclaimer, the term of this patent is extended or adjusted under 35 U.S.C. 154(b) by 301 days.

(21) Appl. No.: 18/653,716

(22) Filed: May 2, 2024

(65) Prior Publication Data

US 2025/0339133 A1 Nov. 6, 2025

(51) Int. Cl.

*A61B 17/00* (2006.01)
*A61B 90/00* (2016.01)
*A61B 90/30* (2016.01)

(52) U.S. Cl.

CPC ........ *A61B 17/00234* (2013.01); *A61B 90/30* (2016.02); *A61B 90/361* (2016.02); *A61B 2017/00305* (2013.01); *A61B 2017/00323* (2013.01)

(58) Field of Classification Search

CPC ... A61B 1/0052; A61B 1/0055; A61B 1/0057; A61B 1/05; A61B 1/3132; A61B 17/00234; A61B 2017/00305; A61B 2017/00323; A61B 2090/309; A61B 34/71; A61B 90/30; A61B 90/361

See application file for complete search history.

(56) References Cited

U.S. PATENT DOCUMENTS 4,651,201 A 3/1987 Schoolman
5,604,531 A 2/1997 Iddan et al.
6,428,469 B1 8/2002 Iddan et al.
9,033,957 B2 5/2015 Caddedu et al.
9,393,076 B2 7/2016 Fowler et al.
9,730,761 B2 8/2017 Fowler et al.
2002/0042562 A1 4/2002 Meron et al.
2005/0288555 A1 12/2005 Binmoeller
2008/0312500 A1 12/2008 Asada et al.
2021/0338355 A1* 11/2021 Yip .......................... A61B 1/05
2023/0016761 A1* 1/2023 Kaiser .................... A61B 34/20

FOREIGN PATENT DOCUMENTS

JP 2000175865 A 6/2000

* cited by examiner

*Primary Examiner* — Scott Luan

(74) *Attorney, Agent, or Firm* — Carter, Ledyard & Milburn LLP

(57) ABSTRACT

An insertion tool for inserting devices during a laparoscopic procedure includes a first housing comprising a joystick module and a circuit board, a second housing comprising a first pulley and a second pulley, an insertable device, a first jacket coupled to the first housing and the second housing, a second jacket coupled to the second housing and an articulating portion. The articulating portion comprises articulating segments. Each of the articulating segments includes a plurality of apertures through which a plurality of lines passes therethrough from the first and second pulleys to sockets located in the insertable device. Movements of the joystick module send signals through the circuit board to motors which displace the first and second pulleys. The displacement of the first and second pulleys ultimately displaces the insertable device via the plurality of lines. Movement of the lines moves the articulating segments in controlled, precise movements during laparoscopic procedures.

17 Claims, 14 Drawing Sheets

16
98
4
94
90
96
18
92
8
8

INSERTION TOOL

TECHNICAL FIELD

This disclosure relates to a system of related devices used during surgery. More specifically, the present disclosure relates to devices used during minimally invasive surgery (also known as laparoscopic surgery).

BACKGROUND

Minimally invasive surgical procedures, e.g., laparoscopic procedures, have dramatically reduced patient recovery times. However, the reduced recovery times have correspondingly resulted in an increase, from a surgeon's perspective, in the complexity of the surgical procedures. This is in part due to relatively small incisions through which a surgeon accesses a surgical site to perform the minimally invasive surgery. The limited access adds to the complexity of the surgical procedures, as surgeons must remotely manipulate sufficiently small instruments through the incisions and must also view the surgical site through the small incisions.

Imaging systems that provide a view of the surgical site for a minimal access surgical procedure typically include an endoscope, e.g., a tubular instrument containing optical lenses and light guides that feed images to an external video camera and a monitor, such as the endoscope discussed in U.S. Pat. No. 4,651,201. Endoscopes, however, have drawbacks. For instance, since the surgeon is generally using both hands to manipulate other instruments used in the procedure, e.g., forceps, scissors, coagulators/cauterizer probes, etc., an assistant is required to hold and orient the endoscope to adjust the view during the procedure. Robotics have recently been introduced to automate the task of orienting the endoscope during minimally invasive surgical procedures, such as the Automated Endoscopic System for Optimal Positioning ("AESOP"). The AESOP uses a robot arm that is directed by spoken commands to orient the endoscope. While the AESOP takes the burden off the assistant and provides a much more stable view of the field, the equipment necessary for the AESOP is complex and occupies a large part of the operating room floor. AutoLap is another system currently on the market, providing an image-guided robotic laparoscopic positioning system. AutoLap interacts with the surgeon's movements in the surgical cavity, guiding the robotic laparoscopic positioner in real time. However, AutoLap still requires a scope to be inserted for the entire duration and the trocar cannula cannot be used for an additional instrument. Therefore, multiple patient incisions are required. In addition, AutoLap requires additional equipment on the outside of the patient which is expensive and also may get in the surgeon's way.

A smaller and simpler robotic endoscope manipulator that can be placed directly over the insertion point was developed at the Institut National de Recherche en Informatique et en Automatiqueinria ("INRIA"). However, the INRIA system as well as other robotic systems fail to address the limited available range of motion about the fulcrum at the abdominal wall through which the endoscope as well as other instruments pass to gain access to the surgical site. The limited range of motion translates into limits with regard to the degree of freedom that the instruments may be oriented toward the surgical site.

Active or hyper endoscope systems have been proposed that generally consist of a multi-link robotic arm with a camera mounted thereon, such as the active endoscope discussed in Japanese Patent 2000175865, which provides additional freedom with respect to orienting the endoscope camera. However, these systems require a dedicated incision for the endoscope to access the surgical site and typically require relatively high voltage to operate the actuators necessary to manipulate the hyper endoscope which from a safety perspective may be problematic when used in surgical procedures. Pill cameras have also been adopted for imaging sections of the small intestine that are out of the reach of a colonoscope, such as the pill camera described in U.S. Pat. Nos. 5,604,531 and 6,428,469. However, pill cameras do not generally include means for orienting the camera; rather, pill cameras merely rely on peristalsis to orient the camera.

Therefore, there is a need for systems and devices for minimal access procedures that do not require an assistant to hold and orient an instrument and that provide additional or greater freedom than is provided with an endoscope or other instrument with regard to orienting the instrument toward the site of interest. There is also a need for systems and devices for minimal access procedures that provide additional or greater freedom with regard to orienting the instrument toward a site of interest than is provided with an active or hyper endoscope that do not require a dedicated access incision into the site for the instrument. Some prior art for fixing surgical tools to the human body internally, include U.S. Pat. No. 9,033,957 discloses a surgical anchor system having an opening and at least one pin to position and orient a surgical tool inside a human body. The surgical anchor is anchored to the lumen of the body cavity by insertion of a single small pin which may be attached providing a hands-free anchor point for other tools while also freeing up the trocar for insertion of additional anchors or providing for insertion of another working surgical tool.

U.S. Publication 2002/0042562 teaches an immobilized in vivo sensing device that has rings attached to it and uses the rings for sewing the device capsule to a desired location in the vicinity of the surgical site. U.S. Publication No. 2005/0288555 discloses a device and method for viewing internal body surfaces without an external attachment. The device is swallowed by the patient or placed with an endoscope and may be secured to the body using securement elements attached to the device such as a barbed hook, a loop or a tab. U.S. Publication 2008/0312500 discloses an endoscope system that includes a camera, a camera side magnet, and a fixing magnet for fixing the camera within the abdominal cavity using fixing magnets and an adhesive layer.

The present disclosure is an improvement to prior art minimal access surgery devices such as U.S. Pat. No. 9,730,761, titled "Insertable Device and System for Minimal Access Procedure," filed Jan. 17, 2012, and U.S. Pat. No. 9,393,076, titled "Insertable Device and System for Minimal Access Procedure," incorporated by reference herein. Both U.S. patents '076 and '761 teach a system including at least one insertable device. The insertable device having an elongated body, two actuators, and a camera. The '761 patent controls the movement of the camera remotely by a control system. U.S. patent '076 has a driving device communicatively connected to the insertable device. The driving device including at least one controller and an image tracking module for tracking the movement of at least one object in a field of view of the camera. Although fixing tools in the human body using certain techniques may be taught in the prior art, they do not teach the novel ideas of the present disclosure.

SUMMARY OF THE DISCLOSURE

In one implementation, an insertion tool for inserting devices during a laparoscopic procedure includes a first housing comprising a joystick module and a circuit board, wherein the joystick module comprises a thumb interface and is coupled to a joystick platform, and the circuit board is positioned closer to the joystick platform relative to the thumb interface. The implementation further includes a second housing comprising a front end and a back end, wherein the second housing comprises a first pulley and a second pulley, the first pulley comprising a first line tension adjustment screw set, and the second pulley comprising a second line tension adjustment screw set, wherein the first pulley is positioned closer to the front end relative to the second pulley. The implementation further includes an insertable device, wherein the insertable device comprises a camera, and a plurality of sockets. The implementation further includes a first jacket coupled to the first housing and the second housing, wherein the first jacket houses one or more cables configured to transport signals from the joystick module to the second housing; and a second jacket coupled to the second housing and an articulating portion, wherein the second jacket houses a plurality of lines, and wherein the articulating portion comprises articulating segments each comprising a plurality of apertures, the plurality of lines each passing through one of the plurality apertures towards the second housing, via the second jacket, to enable controllable displacement of the articulating segments, wherein one of the plurality of lines is coupled to the first pulley, and another of the plurality of lines is coupled to the second pulley, and the plurality of lines have a ball-shaped end that is coupled to one of the plurality of sockets of the insertable device, thereby coupling the articulating portion to the insertable device.

One or more of the following features may be included. The insertion tool may include the articulating segments having a concave side and a convex side. The insertion tool may include the plurality of apertures comprising a first aperture, a second aperture, a third aperture, a fourth aperture, and a fifth aperture, wherein the first, second, third, and fourth apertures are positioned substantially 90 degrees away from one another, and the fifth aperture is located in between the first, second, third, and fourth apertures and is larger than the first, second, third, and fourth apertures. The insertion tool may include the first pulley having a first arm and a second arm coupled to the first line tension adjustment screw set, and the second pulley further comprising a third arm and a fourth arm coupled to the second line tension adjustment screw set. The insertion tool may include the articulating segments being arranged so that the concave side of each articulating segment is in contact with the concave side of another articulating segment, while the convex side of each articulating segment is in contact with the convex side of another articulating segment. The insertion tool may include the first pulley comprising a first rotation plane and the second pulley comprises a second rotation plane, and the first rotation plane and the second rotation plane are substantially perpendicular to each other. The insertion tool may include the first pulley and the first rotation plane displacing the plurality of lines in a substantially vertical direction, and the second pulley and the second rotation plane displace the plurality of lines in a substantially horizontal direction. The insertion tool may include a first motor and a second motor, wherein the first motor is coupled to a first worm gear, and the second motor is coupled to a second worm gear. The insertion tool may include the first worm gear being coupled to the first pulley, and the second worm gear being coupled to the second pulley. The insertion tool may include the joystick module being configured to displace the first motor and the second motor. The insertion tool may include a tube, the tube comprising a plurality of notches, wherein the plurality of notches is configured to restrict movement of the plurality of lines and to prevent the plurality of lines from contacting one another. The insertion tool may include the second jacket further comprising pathways, wherein each pathway is configured to enclose one of the plurality of lines, and wherein each one of the plurality of pathways aligns with one of the plurality of apertures of the articulating segments. The insertion tool may include the first housing further comprising a strain relief located closer to the circuit board relative to the joystick module. The insertion tool may include the articulating segments being configured to displace the insertable device following movement of the plurality of lines while maintaining the position of the insertable device following displacement. The insertion tool may include the second housing further comprising a first mounting bracket coupled to the first worm gear, and a second mounting bracket coupled to the second worm gear.

BRIEF DESCRIPTION OF THE DRAWINGS

Various embodiments in accordance with the present disclosure are with reference to the drawings, in which.

DETAILED DESCRIPTION OF THE PREFERRED EMBODIMENTS

Figure 1:
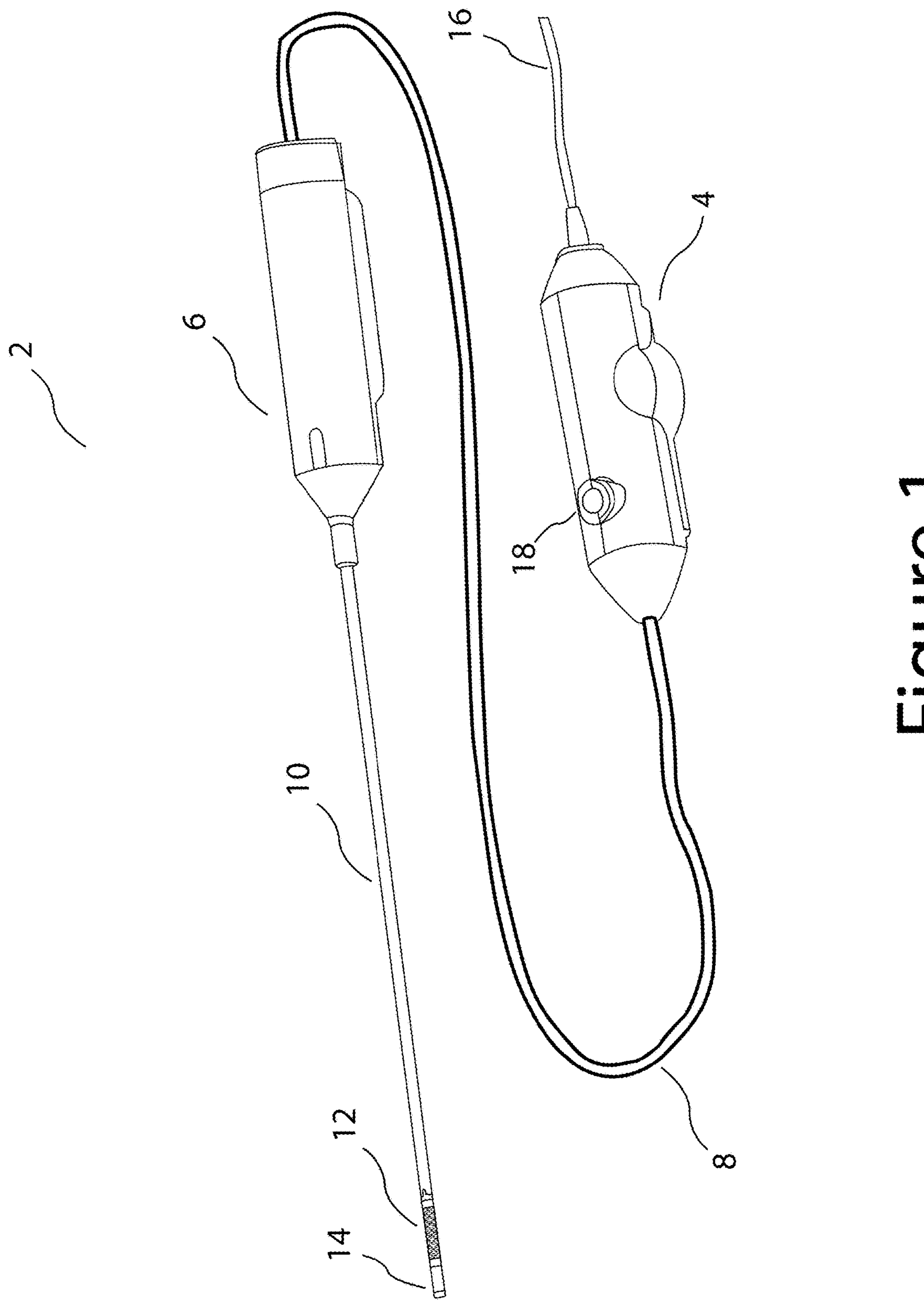
FIG. 1 illustrates an example of an insertion tool in a perspective view.

Referring to FIG. 1, there is shown an insertion tool 2 for inserting devices during a laparoscopic procedure. Insertion tool 2 may include a first housing 4 and a second housing 6.

A first jacket 8—which may be made of plastic (e.g., polyurethane, polyvinyl chloride, thermoplastic elastomer, etc.), textiles, and/or fabrics—may house lines, wires, cables, cords, and/or ropes. First jacket 8 may couple the first housing 4 to the second housing 6 so that the lines, wires, cables, cords, and/or ropes housed by first jacket 8 extend from the first housing 4 to the second housing 6. First jacket 8 may facilitate the transportation of electrical signals and/or mechanical energy between first housing 4 and second housing 6. Electrical power may come from wires or cables housed in a third jacket 16.

A second jacket 10 may be coupled to the second housing 6 and an articulating portion 12. Second jacket 10 may be composed of a rigid material, while articulating portion 12 may be flexibly displaceable. Articulating portion 12 may be coupled to an insertable device 14. The insertable device 14 may include a housing having a camera. The housing of insertable device 14 may also house other mechanical or electronic parts, including a lens-washing device, lights, and sensors, among other items.

First housing 4 may be coupled to third jacket 16. Third jacket 16 may also be coupled to an electrical power source. The electrical power source (not shown) may include a battery, a computer, an outlet, or another electrical device capable of transmitting power through third jacket to parts of first housing 4. First housing 4 may further include a thumb interface 18. The thumb interface 18 may be a joystick handle or a pressure sensor capable of transmitting directional inputs or information in the form of electrical signals to second housing 6. Thumb interface 18 may be connected to a circuit board inside first housing 4 to enable transmission of electrical signals based on input from a user applying forces to thumb interface 18.

Figure 2A:
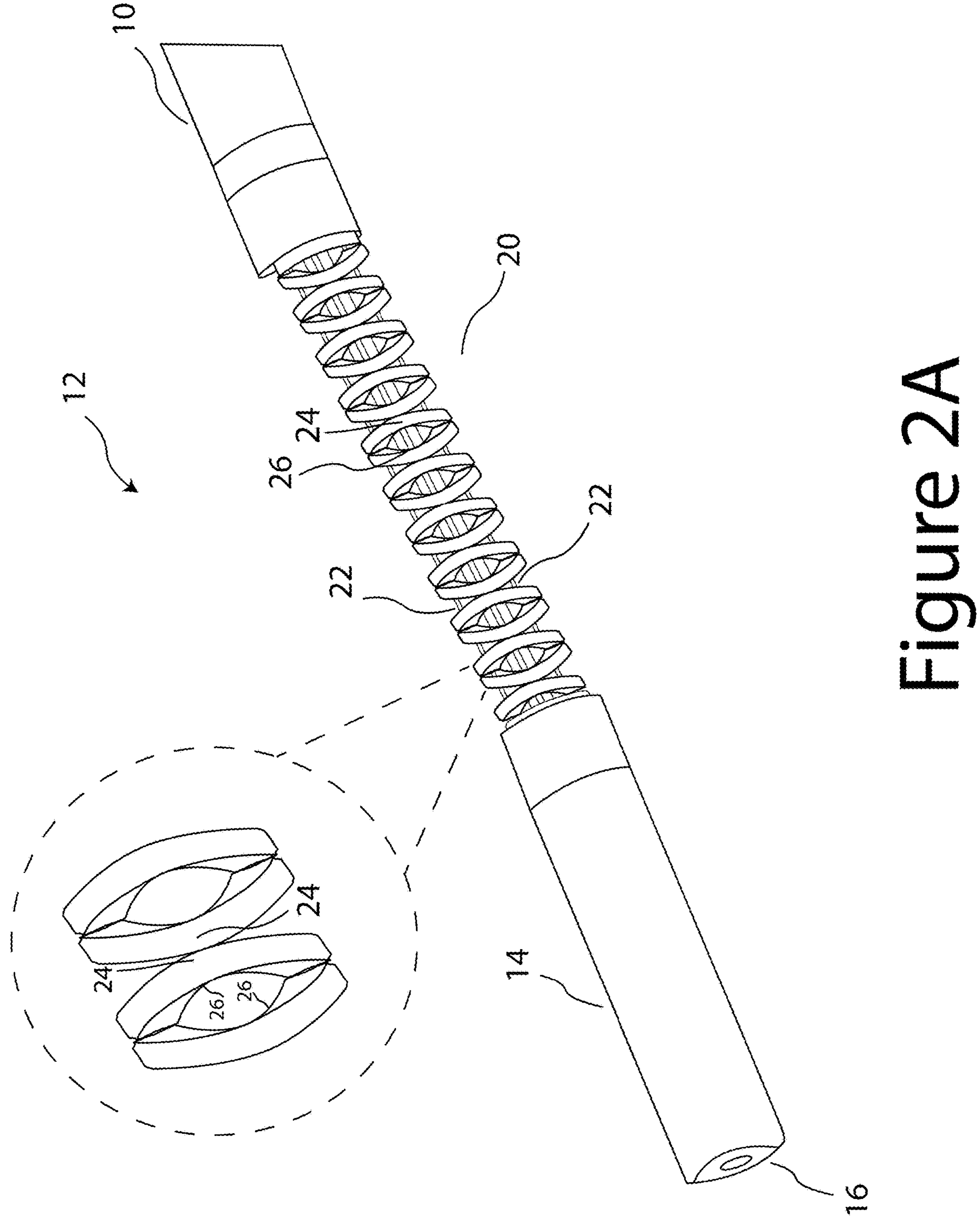
FIG. 2A illustrates an example of an insertion tool with a closer view of the tool's articulating portion, articulating segments, and insertable device.

Referring to FIG. 2A, there is shown articulating portion 12 in a perspective view. Articulating segments 20 are shown as ring-like structures occupying the distance between second jacket 10 and insertable device 14. Insertable device 14 may have a camera 16 therein. Camera 16 may have a lens that to capture images and/or videos in planes or views that insertable device 14 is able to access. Camera 16 may further include photo transmission capabilities through wired or wireless means. A plurality of lines 22 (which may be composed of metal, plastic, textiles, fibers, a rope made of natural materials, or a combination of any of these materials) may couple articulating segments 20. The lines may pass through apertures (not shown) of the articulating segments from second jacket 10 and may terminate at sockets (not shown) within insertable device 14. Articulating segments 20 may be curved, ring-like structures with a convex side 24 and a concave side 26. Articulating segments 20 may be arranged so that their concave sides 26 are in contact with one another, while their convex sides 24 are concurrently in contact with one another. A portion of the second jacket 10 may be in contact with the concave side of one of the articulating segments 20. The plurality of lines 22 may be flexible and may displace articulating segments 20 following forces which may be applied to the plurality of lines 22. The plurality of lines 22 may be at least two lines. Each of the plurality of lines may pass through one of the apertures.

Figure 2B:
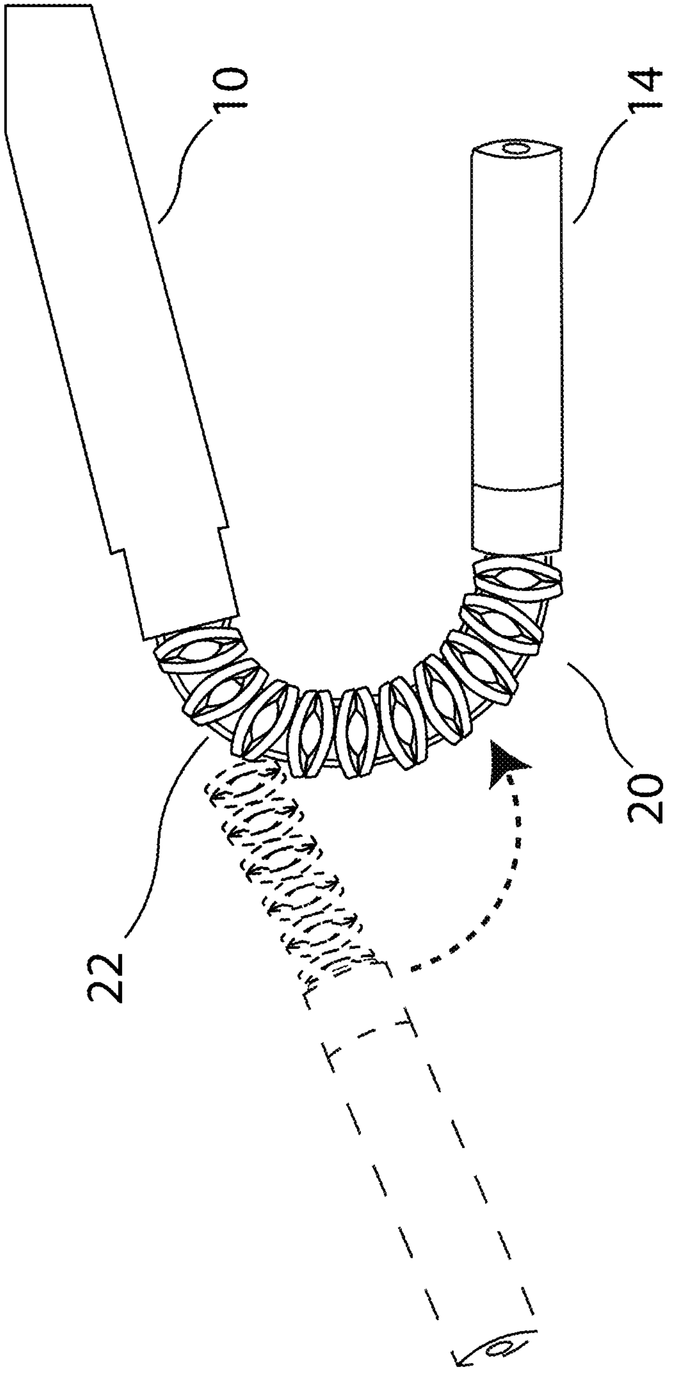
FIG. 2B illustrates an example of an insertion tool with its articulating portion displaced in a parabolic path.

For instance, as exemplified in FIG. 2B, if one of the plurality of lines experience a force which displaces the line in a left-handed direction, the line would subsequently displace the articulating segments 20 and the insertable device 14 towards the same left-handed direction. While changing directions and reaching a predetermined position, articulating segments 20 may be arranged to resemble a curved, parabolic path to ensure a smooth, controllable displacement of the insertable device 14 during laparoscopic surgery. Articulating segments 20 may displace insertable device 14 following forces applied via the plurality of lines 22. The plurality of lines 22 may maintain a displaced position of insertable device 14 when the plurality of lines 22 do not experience any force input.

Figure 3:
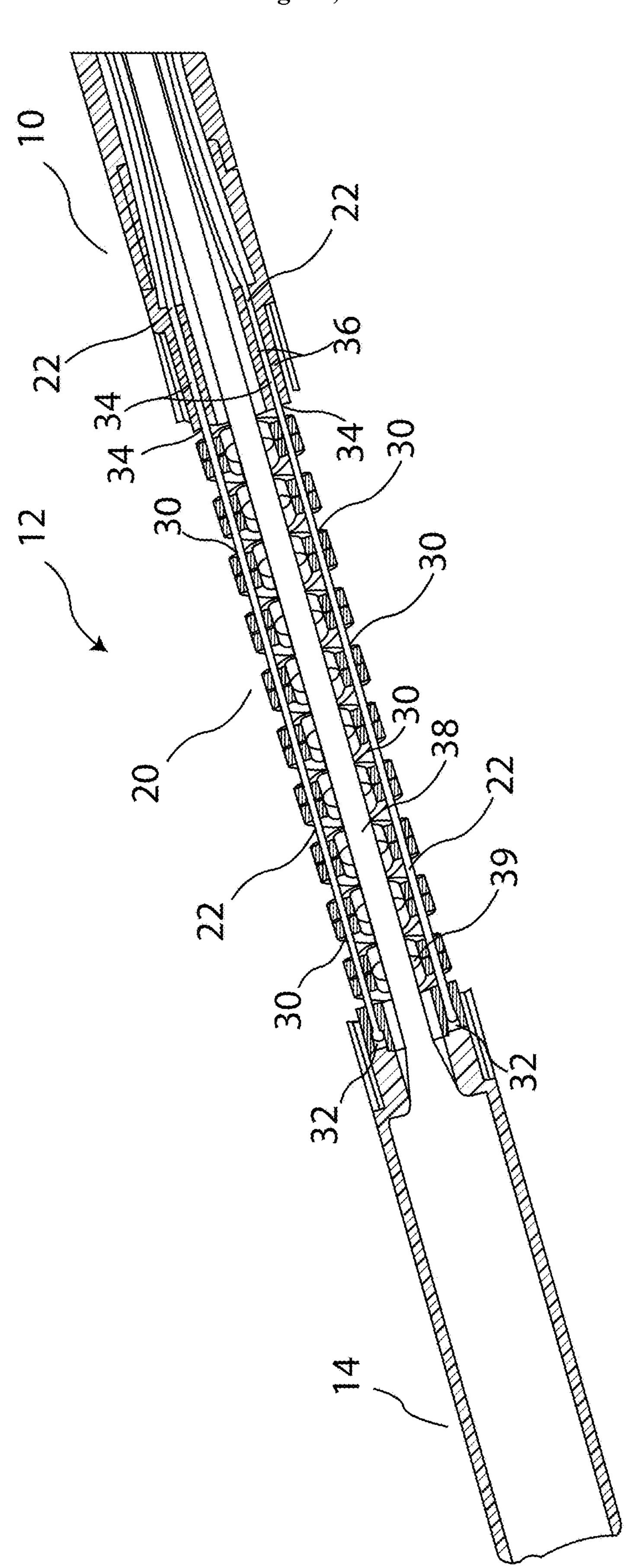
FIG. 3 illustrates an example of an insertion tool with its articulating portion and its insertable device viewed in a cross-section view.

Referring to FIG. 3, there is shown a cross-sectional view of FIG. 2A along a longitudinal section of insertable device 14, articulating portion 12, and second jacket 10. The plurality of lines 22 may pass through apertures 30 of articulating segments 20. The plurality of lines 22 may stem from second housing 6 (not shown in FIG. 3) and second jacket 10 and then couple with sockets 32. The coupling of lines 22 with sockets 32 may be in the form of a ball-and-socket joint, which would enable displacement of insertable device 14 when articulating portion 12 is displaced via movement of the plurality of lines 22. The coupling of lines 22 with sockets 32 also couples insertable device 14 to articulating portion 12. Other joint-like configurations may be included in sockets 32, including, for example, hinge joints, saddle joints, and pivot joints, and condyloid joints. Pathways 34, which are defined by a plurality of walls 36 of second jacket 10, align the plurality of lines 22 with apertures 30 when the plurality of lines 22 are substantially straight. Sockets 32 are also aligned with apertures 30 when the plurality of lines 22 are substantially straight. Positioning of insertable device 14 may depend on the displacement of lines 22. Insertable device 14 may maintain a particular orientation through coupling forces facilitated by the coupling of lines 22 with sockets 32. The coupling forces may enable insertable device 14 to face nearly any orientation or plane during operation of components of second jacket 10. A spine 38 may originate from second jacket 10 through an interior space 39 defined by articulating segments 20 towards insertable device 14. Spine 38 may be integrally connected with insertable device 14 or couple to insertable device 14 through conventional mechanical coupling means (not shown). Spine 38 may be made of flexible material that would, for example, enable it to curve and define a parabolic path. Spine 38 is configured to be displaced as articulating segments 20 move as a result of displacement of lines 22.

Figure 4A:
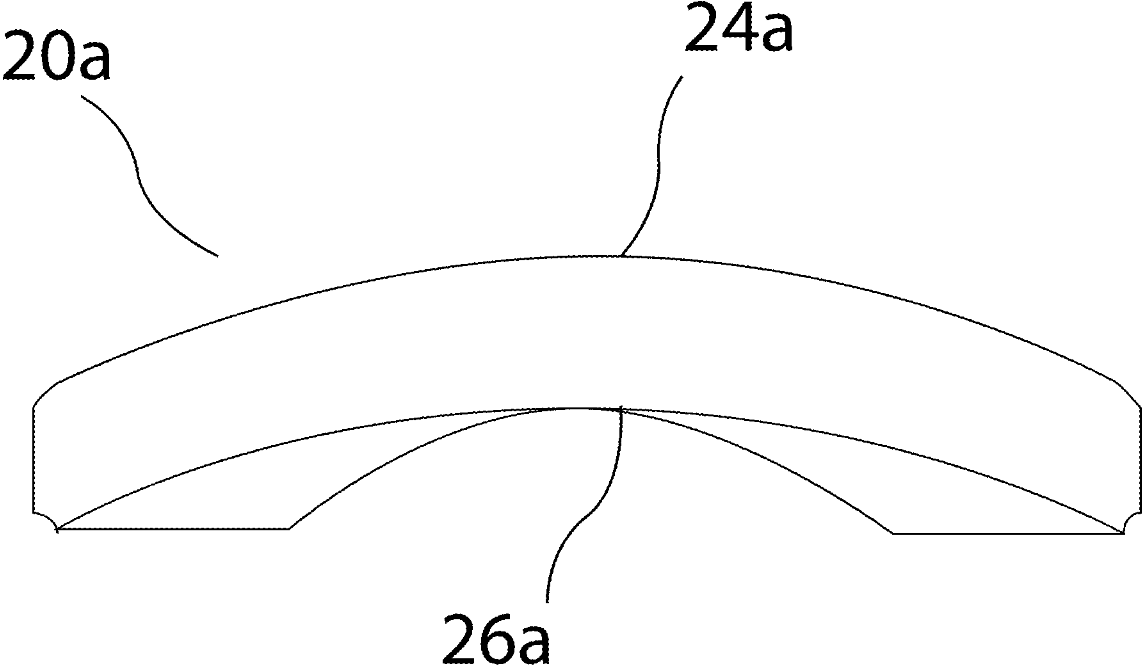
FIG. 4A illustrates an example of an articulating segment in a profile view.
Figure 4B:
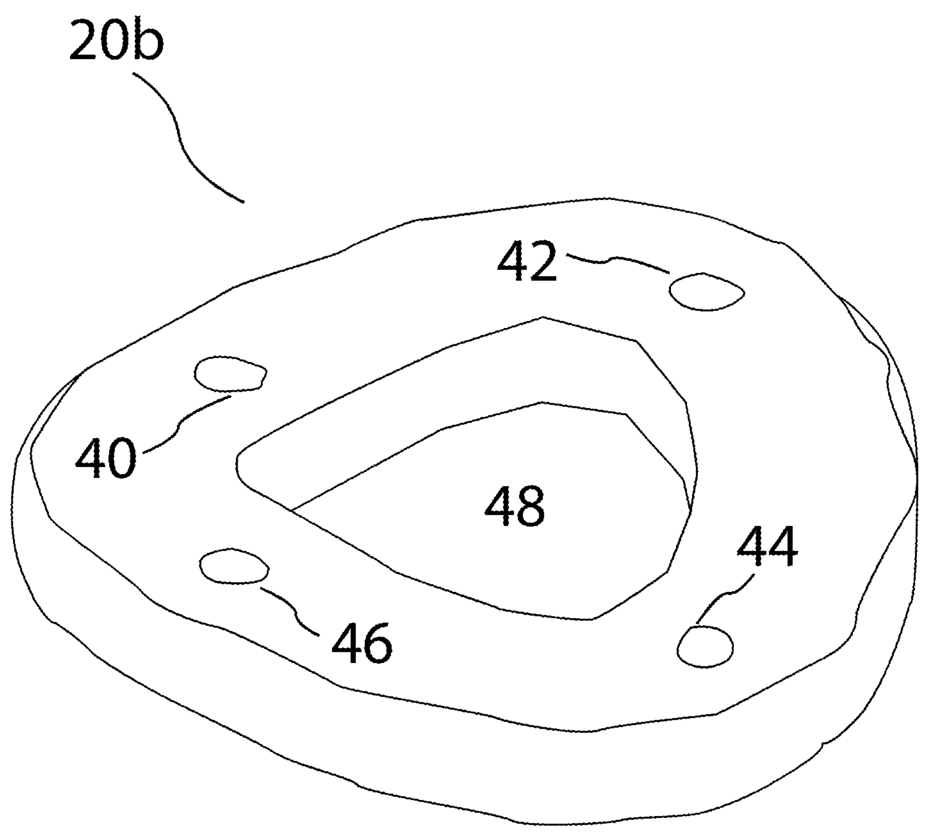
FIG. 4B illustrates an example of an articulating segment in a perspective view.
Figure 4C:
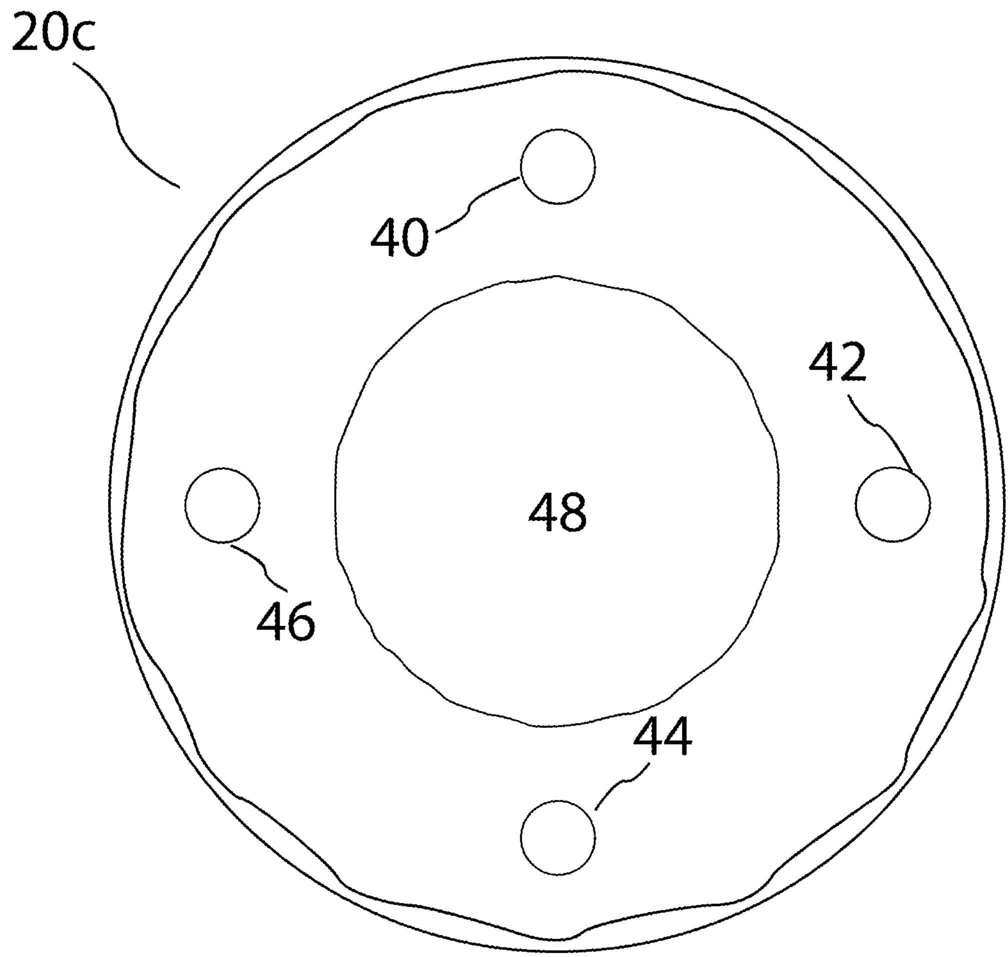
FIG. 4C illustrates an example of an articulating segment in a plane perpendicular to the plane of FIG. 4A, thereby showing the front or back of the articulating segment.

Referring to FIG. 4A, there is shown a profile view of an articulating segment 20*a*. Referring to FIG. 4B, there is shown a perspective view of an articulating segment 20*b*. Referring to FIG. 4C, there is shown an articulating segment 20*c* in a plane perpendicular to the plane of FIG. 4A, thereby showing the front or back of articulating segment 20*c*. Articulating segments 20*a*, 20*b*, and 20*c* may substantially resemble articulating segments 20. Articulating segment 20*a* may have a convex side 24*a* and a concave side 26*a*. Articulating segments 20*a*, 20*b*, and 20*c* may have a first aperture 40, a second aperture 42, a third aperture 44, a fourth aperture 46, and a fifth aperture 48 (not shown in FIG. 4A). First through fourth apertures 40, 42, 44, and 46 may be positioned substantially 90 degrees away from one another (e.g., a 12'o clock position, a 3'o clock position, a 6'o clock position, and a 9'o clock position). Apertures 40, 42, 44, and 46 may be of substantially the same diameter. Fifth aperture 48 may be positioned in between apertures 40, 42, 44, and 46. Fifth aperture 48 may also have a larger diameter than the first through fourth apertures 40, 42, 44, and 46. Lines 22 (not shown) may pass through first through fourth apertures 40, 42, 44, and 46 to enable and/or restrain movement of articulating segments 20*a*-20*c*. Spine 38 (not shown) may pass through fifth aperture 48 and be displaced in substantially similar directions as lines 22 so that the edges of first through fifth apertures 40, 42, 44, 46, and 48 make little to no frictional contact with lines 22 and spine 38.

Figure 4D:
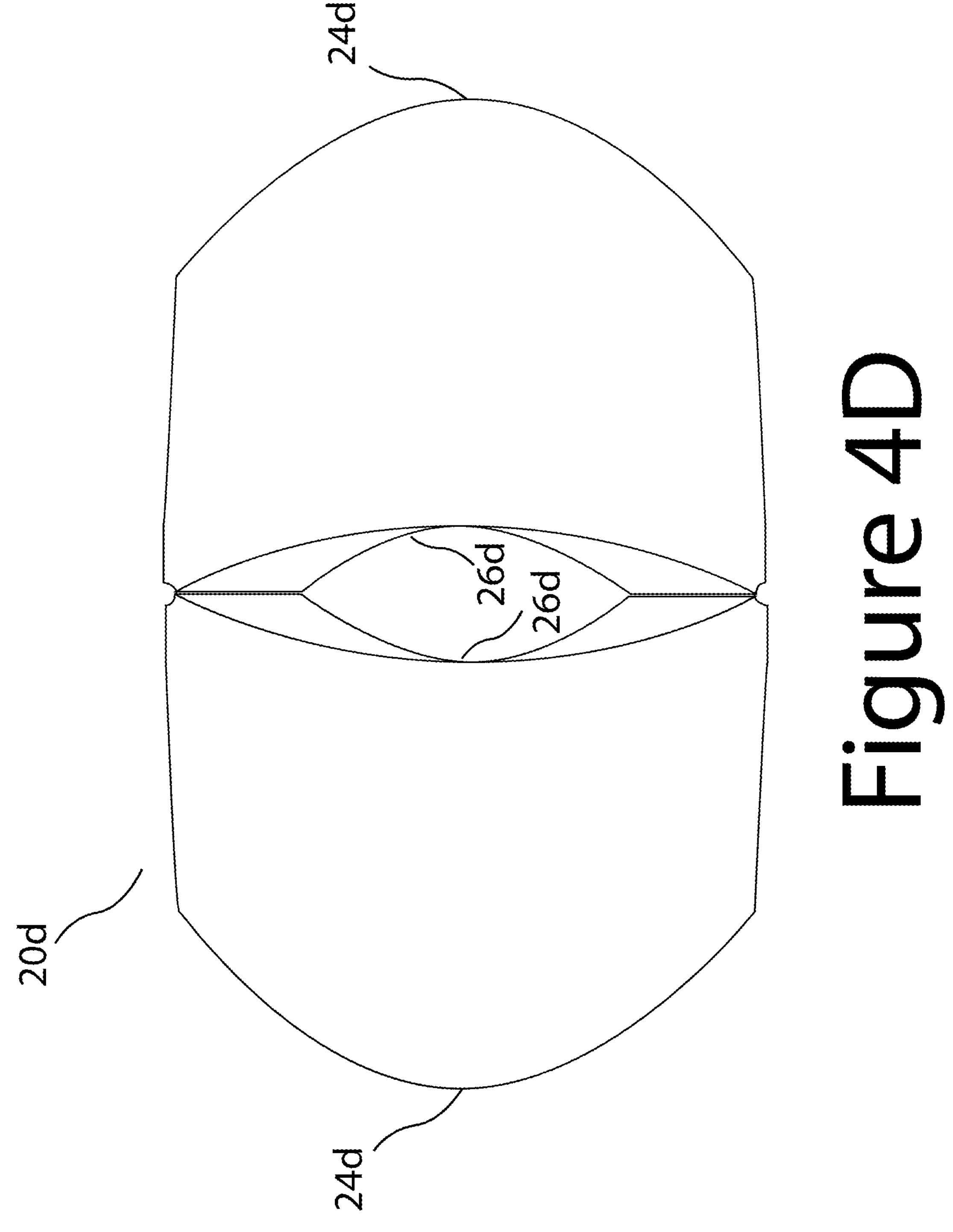
FIG. 4D illustrates an example of an alternative embodiment of an articulating segment.

Optionally, articulating segments 20 may also, for example, substantially resemble articulating segments 20D shown in FIG. 4D. That is, FIG. 4D presents an alternative embodiment of articulating segments 20, labelled as 20*d*. The distance between a convex side 24*d* and a corresponding concave side 26*d* of articulating segments 20*d* may be larger than the distance between 24*a* and 26*a* (shown in FIG. 4A) to make each aspect of articulating segments 20*d* larger. Articulating segments 20*d*, having larger pieces, may decrease manufacturing costs by having insertion tool 2 require fewer articulating segments 20 to manipulate insertable device 14. Articulating segments 20*d* may also be more appropriate for larger-sized insertion tools (e.g., a larger version of insertion tool 2 for larger surgery sites and/or larger insertable devices). The front/back view of articulating segments 20*d* may substantially resemble the view of FIG. 4C.

Figure 5A:
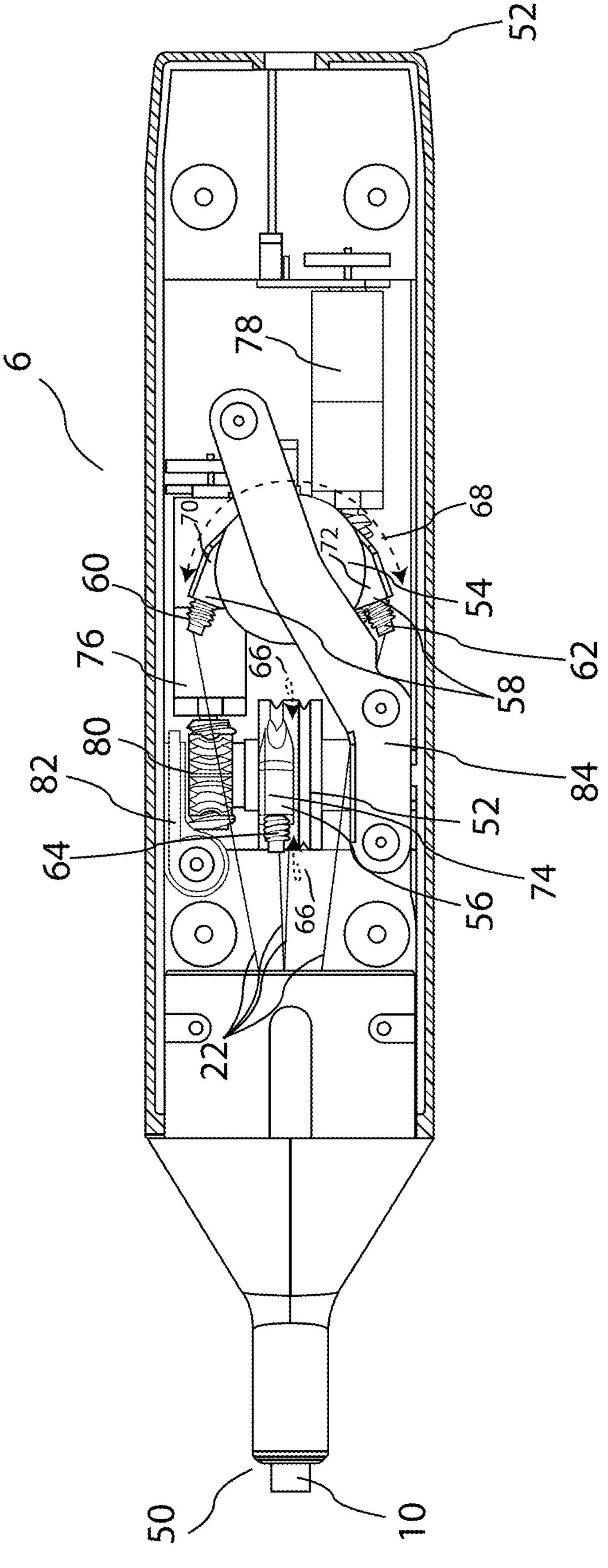
FIG. 5A illustrates an example of an insertion tool's second housing in a cross-section view.

Referring to FIG. 5A, there is shown a cross-sectional view of the second housing 6 of FIG. 1. Second housing may have a front end 50, from which the second jacket 10 may protrude therefrom. Second housing 6 may also have a back end 52 from which first jacket 8 (not shown) may protrude therefrom. In second housing 6, there is shown a first pulley 52 and a second pulley 54. The first pulley 52 may have a first line tension adjustment screw set 56 and the second pulley 54 may have a second line tension adjustment screw set 58. Each of the screw sets 56 and 58 may include two holding screws (labelled 60, 62, and 64, with the fourth holding bolt not shown in FIG. 5A). Holding bolt 64, along with the unshown holding bolt which may be located on an opposite side of first pulley 52, may couple with lines 22 and exert tensional or compressional forces on lines 22 via rotation of first pulley 52 in one axis. First pulley 52 and lines 22 may be coupled through welding, snap-fitting, compression screwing, or compression pressing. Holding screws 60 and 62 of second pulley 54 may couple with lines 22 and exert tensional or compressional forces on lines 22 via rotation of second pulley 54 in an axis perpendicular to the rotational axis of first pulley 52. For example, first pulley 52 may rotate to exert forces on two of lines 22, wherein the two lines are located on a same, first plane. Forces exerted on these lines by first pulley 52 may then cause articulating portion 12 (not shown in FIG. 5A) to displace insertable device 14 in, for instance, an up or down direction (or a north-south direction). Within this same example, second pulley 54 may rotate to exert forces on two of other lines 22, wherein the two other lines are located on a second plane that is perpendicular to the first plane so as to displace insertable device 14 in, for instance, a left or right direction (or an east-west direction). Second pulley 54 and lines 22 may be coupled via welding, snap-fitting, compression screwing, or compression pressing. When combining rotational displacements of first pulley 52 and second pulley 54, insertable device 14 may, for instance, be displaced into any plane. First pulley 52 may be positioned closer to first end 50 than second pulley 54 to ensure lines 22 do not entangle into one another as well as to prevent first pulley 52 and second pulley 54 (and their respective tension adjustment screw sets 56 and 58) from contacting one another as they rotate.

Graphically, a first rotation plane 66 is illustrated via dashed arrows indicating permitted rotational movement of first pulley 52. A second rotation plane 68 is illustrated via dashed arrows indicating permitted rotational movement of second pulley 54. First rotation plane 66 and second rotation plane 68 may be substantially perpendicular to each other. First pulley 52 and the first rotation plane 66 may displace lines 22 in a substantially vertical direction. Second pulley 54 and the second rotation plane 68 may displace lines 22 in a substantially horizontal direction.

First pulley 52 may have a first arm 74 and a second arm (located on a side of the first pulley opposite of the side of the first pulley where the first arm is coupled thereto; not shown in FIG. 5A). These two arms may be coupled to first line tension adjustment screw set 56. The arms permit a wider rotation diameter (i.e., a larger span of rotation) for the holding screws of first pulley 52 to exert compressional and/or tensional forces on lines 22. Second pulley 54 may have a third arm 70 and a fourth arm 72 coupled to second line tension adjustment screw set 58. Third and fourth arms 70 and 72, like for first pulley 52, increase the span of rotation of second tension adjustment screw set 58 so as to permit additional ranges of forces that second pulley 54 may exert on lines 22.

Second housing 6 may include a first motor 76 and a second motor 78. Second motor 76 may be coupled to a first worm gear 80, whereas second motor 78 may be coupled to a second worm gear (not shown in FIG. 5A). First worm gear 80 may be coupled to first pulley 52. The second worm gear may be coupled to second pulley 54. Displacement of first motor 76 may cause first worm gear 80 to rotate. The rotation of worm gear 80 then may cause first pulley 52 to rotate. That is, control of displacement of first motor 76 leads to control of the rotation of worm gear 80 and first pulley 52. A similar example for second motor 78 may also apply. Controlling the movement of second motor 78 may lead to control of the second worm gear (not shown), which may ultimately control the rotation of second pulley 54. Control of first pulley 52 and second pulley 54 may include rate of rotation and/or rotational positioning. First worm gear 80 may also be coupled to a first mounting bracket 82, whereas the second worm gear may be coupled to a second mounting bracket 84. First mounting bracket 82 and second mounting bracket 84 may each mount first worm gear 80 and the second worm gear, respectively, to inner walls of second housing 6. Optionally, first motor 76 and second motor 78 may be housed in first housing 6 so that these motors may be further away from a surgery's sterile field. Minimizing the number of foreign objects in the surgery's sterile field would yield less risks in causing infections, better maintain sterility, increase patient safety, and, in some cases, comply with specific medical standards.

Figure 5B:
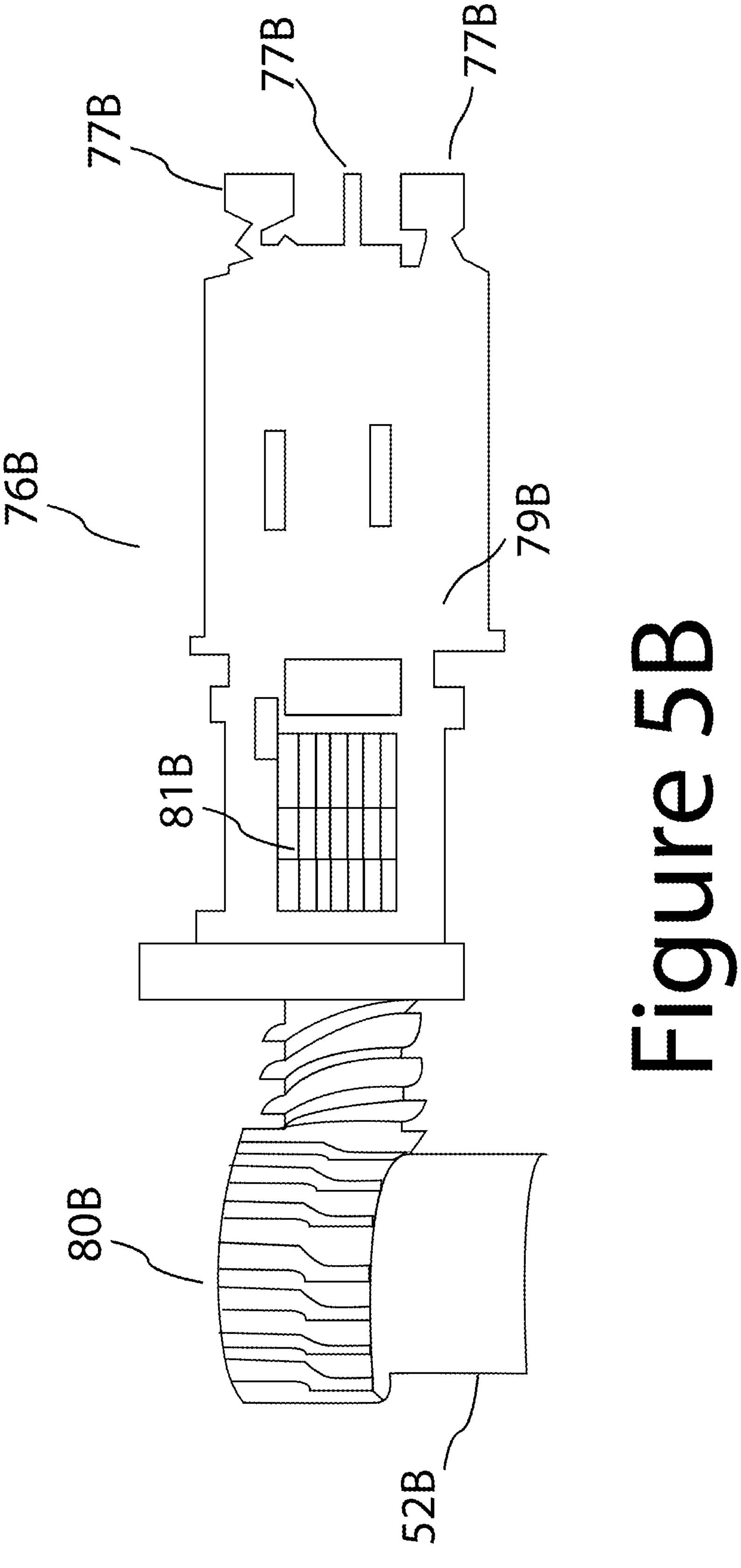
FIG. 5B illustrates an example of a motor which may be within the second housing.

Referring to FIG. 5B, there is shown an example of a motor 76B which may be within the second housing. Motor 76 may include some or all aspects of motor 76B. Motor 76B may include signal connectors 77B and a motor housing 79B. Signal connectors 77B may be coupled with a signal generating device (not shown) so that signal connectors 77B may receive electrical signals from the signal generating device. Examples of signal generating devices may include electronic joysticks, trackballs, touchpads, directional pads, steering wheels, and other directional or pressure-sensitive surfaces. Signal connectors 77B may receive electrical signals and may then cause motor parts 81B within motor housing 79B to start functioning. Motor parts 81B may include a shaft (not shown) capable of rotating. Motor parts 81B may then cause a worm gear 80B to rotate. Worm gear 80B may then cause a part of a pulley 52B to rotate. Pulley 52B may be, for example, a part of first pulley 52 in FIG. 5A. That is, by way of example, if pulley 52B were a part of first pulley 52, and pulley 52B were rotated by worm gear 80B following movement caused by motor 76*b*, then first pulley 52 would displace lines 22 by pulling or pushing onto lines 22 in a substantially vertical plane. If pulley 52B were part of second pulley 54, then rotation of worm gear 80B would cause lines 22 to be displaced through tensional and/or compressional forces (exerted by second pulley 54) within a substantially horizontal plane (or a plane that is substantially perpendicular to the plane outlined for first pulley 52).

Figure 6:
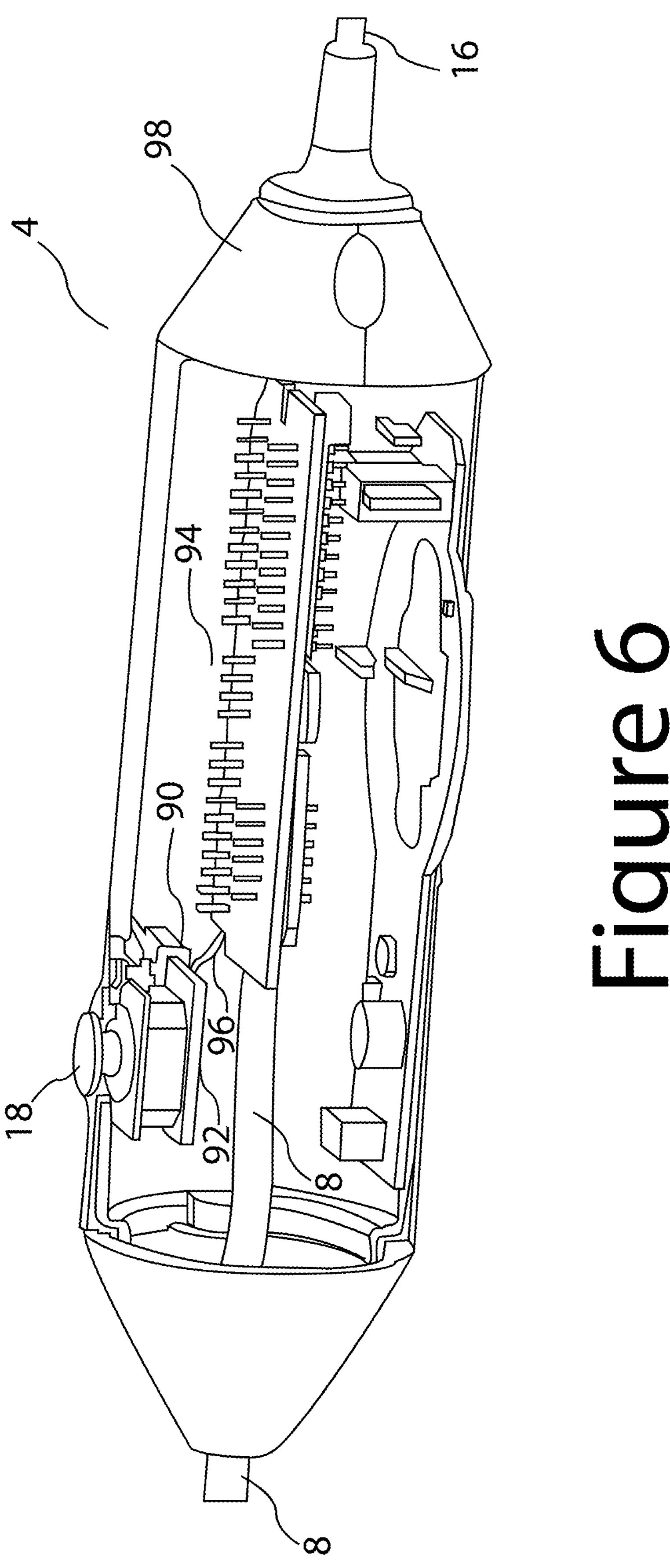
FIG. 6 illustrates an example of an insertion tool's first housing in a perspective, cross-section view.

Referring to FIG. 6, there is shown a perspective, cross-section view of first housing 4. First housing 4 may include first jacket 8 extending from one side therefrom, and third jacket 16 extending from another side of first housing 4. Thumb interface 18 may extend from a face of first housing 4. Thumb interface 18 may be a joystick module 90 attached to a joystick platform 92. Joystick module 90 may generate electrical signals which may be sent to signal connectors 77B of motor 76B. Joystick platform 92 may be a surface on which joystick module 90 may be elevated within the inner walls of first housing 4. Joystick platform 92 may be coupled to a portion of the inner walls of first housing 4. For instance, joystick platform 92 may be coupled to a portion of the inner walls of first housing 4 so that joystick platform 92 may hold joystick module 90 at a height in which thumb interface may protrude from first housing 4. The exemplary position of joystick platform 92 may also provide space for a circuit board 94 to be positioned within first housing 4 in which circuit board 94 is coupled to joystick module 90 via a cable 96. Cable 96 may be configured to send electrical signals transmitted by a user's operation of thumb interface 18 to circuit board 94. Circuit board 94 may then transmit signals through first jacket 8 to cause controlled displacement of motors (labelled 76 and 78 in FIG. 5A) within second housing 6 (see FIG. 5A). Control of thumb interface 18 is thereby configured to control displacement of first and second motors 76 and 78. The control of first and second motors 76 and 78 may then control displacement of lines 22 and, ultimately, displacement of insertable device 14 in minute, accurate increments. Minute, accurate increments of displacement ensure safe surgical procedures and sufficient control for a medical professional to accurately manipulate insertable device 14 during crucial surgical procedures. In addition to signals sent through first jacket 8, circuit board 94 may transmit signals through third jacket 16 to a computer (not shown in FIG. 6) to enable a user to read information about or pertaining to the signals on a user interface (not shown in FIG. 6).

To relieve stress from cable connections housed within first through third jackets 8, 10, and 16, a strain relief 98 may be included. Strain relief 98 may be located at a base of first housing 4 (e.g., near third jacket 16). For example, strain relief 98 may be located closer to circuit board 94 relative to joystick module 90 in order to relieve stress of multiple wires stemming from the circuit board while minimizing the distance the wires would traverse between circuit board 94 and strain relief 98. Strain relief 98 may be in the form of metallic connectors and/or grips to provide tensile strength. Strain relief 98 may also be in the form of a segmented sleeve. To the extent strain relief 98 is in the form of the segmented sleeve, the segmented sleeve may be configured to accommodate other laparoscopic equipment, including, but not limited to, suction equipment, irrigation equipment, hand-assist devices, closure devices, insufflation devices, and/or other surgical instruments. Strain relief 98 may be made of a suitable material, which may include aluminum, brass, nylon, polymers, and/or steel.

Optionally, instead of motors 76 and 78, levers or a rotating-ring may be used to cause first worm gear 80 and second worm gear to rotate, and thereby to rotate first pulley 52 and second pulley 54, respectively. The levers or the rotating-ring may be displaced via electrical signals from joystick module 90.

Figure 7:
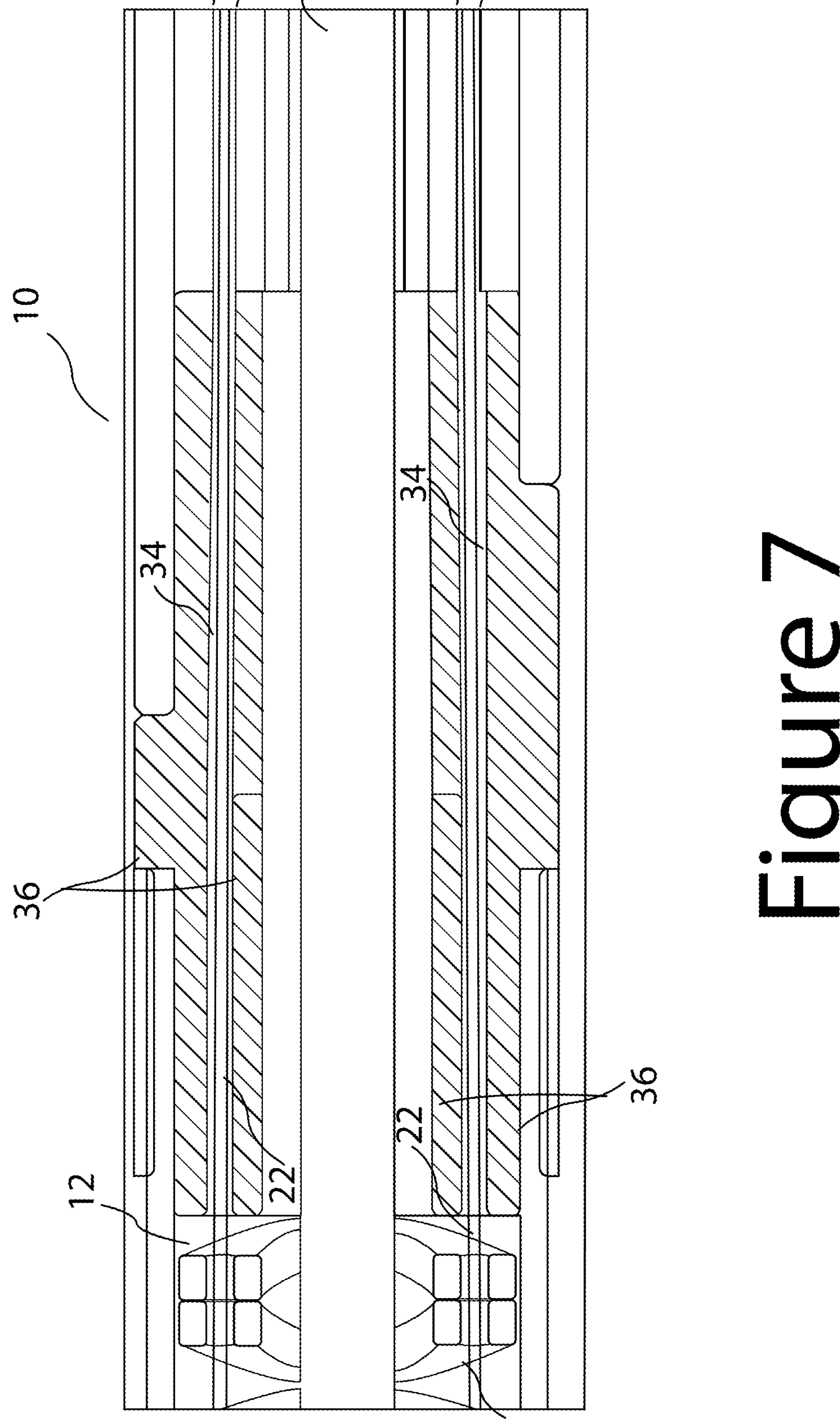
FIG. 7 illustrates an example of an insertion tool and its second jacket in a cross-section view.

Referring to FIG. 7, there is shown a cross-section of second jacket 10 with some articulating segments 20 of articulating portion 12 shown. Lines 22 may pass through apertures of articulating segments 20 and in between walls 36. Walls 36 may constrain lines 22 to run through pathways 34. Spine 38 may substantially extend through the middle of second jacket 10 and passes through apertures of articulating segments 20. Pathways 34 may be defined by tubes 100 which may encase lines 22.

Figure 8:
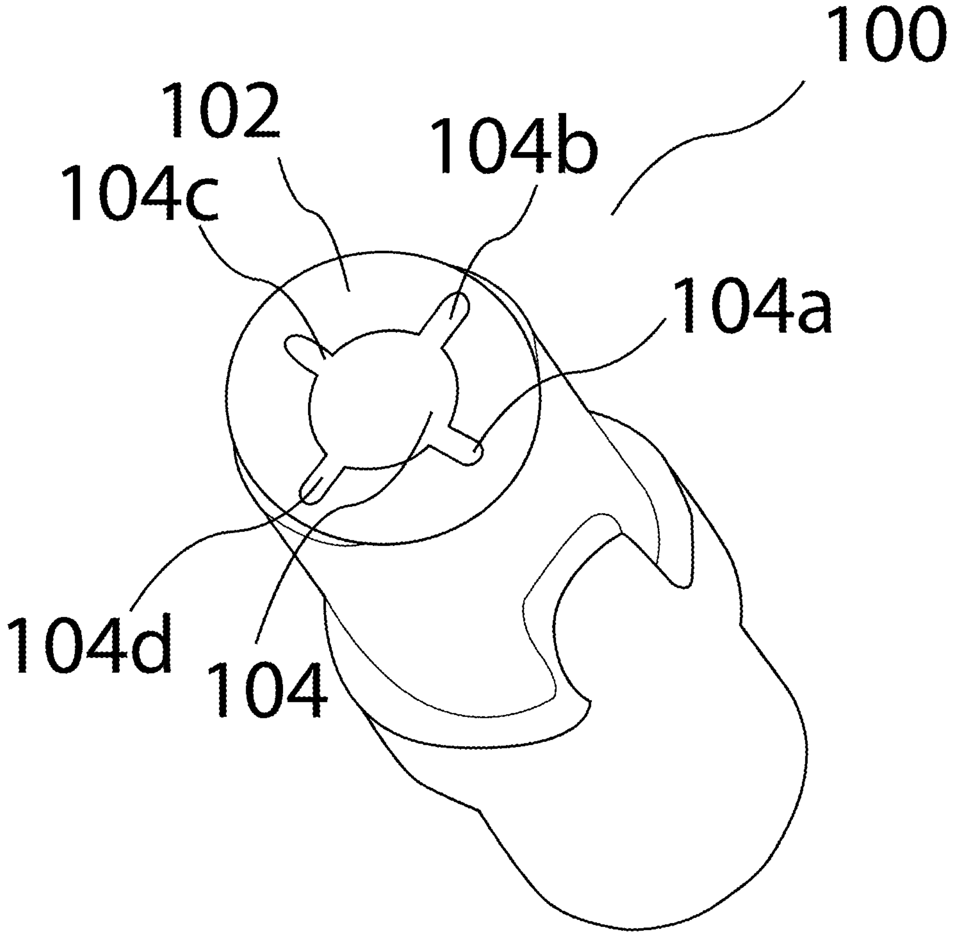
FIG. 8 illustrates an example of a portion of an insertion tool's tube.

Referring to FIG. 8, there is shown a portion of tube 100, where an end 102 of tube is visible. End 102 may have an outlet 104 through which spine 38 and lines 22 (not shown) may pass therethrough. Outlet 104 may further include notches 104*a*, 104*b*, 104*c*, and 104*d*. Each of the notches 104*a*-104*d* is configured to restrict movement of the plurality of lines 22 and to prevent the lines 22 from contacting one another during operation of the insertion tool 2. The notches 104*a*-104*d* also prevent lines 22 from escaping from outlet 104 and from escaping tube 100. Notches 104*a*-104*d* may be substantially aligned with apertures of articulating segments (not shown).

Figure 9:
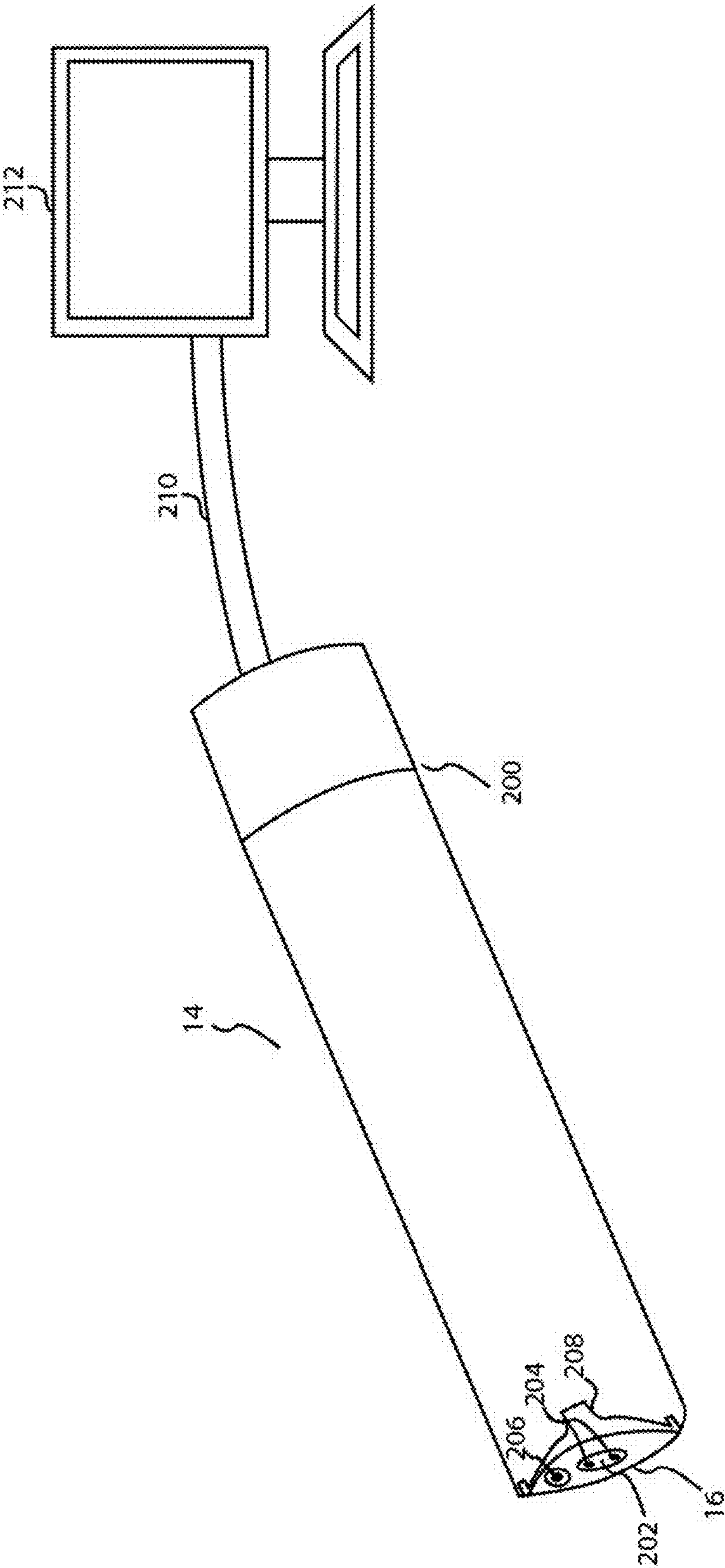
FIG. 9 illustrates an example of an insertable device.

Referring to FIG. 9, there is shown an example of insertable device 14, comprising camera 16, which may be a high definition camera and/or a camera capable of providing an exploded view; a flexible housing 200 capable of being elastically displaced while operating during a laparoscopic procedure; a sensor 202 to sense predetermined paths, patterns, visual signals, lights, shades, and/or other particular tissue structures; at least two LED lights 204 for illuminating a laparoscopic site and to aid sensor 202 in sensing visual patterns and/or cues (two LEDs also reduce shadows that would result from a single LED); a lens flush 206 which may periodically eject lens flush fluid (e.g., sterile saline solution) to clean camera 16, maintain camera clarity, and maintain visual capabilities of sensor 202; and a motor 208 for moving camera 16 in relation to flexible housing 200. Motor 208 may have pan and tilt capabilities, which may include maintaining camera 16 so as to obtain the same horizon regardless of camera 16 position. Insertable device 14 may also include cord or cords 210 exiting out of a back of the insertable device. Cords 210 may provide signal and image information from camera 16 and sensor 202 to an external unit 212. External unit 212 may be a computer, a tablet, a cell phone, a monitor, or a projector. External unit 212 may also be placed on a shelf and include software, a test panel, and/or an interface for manual control of motor 208.

Operation of insertion tool 2 may include preparing external unit 212 for connection and/or communication with insertion tool 2. Insertion tool 2 may then be tested by an operator to ensure that insertable device 14 is displaced according to the operator's control of thumb interface 18. The operator may then insert insertable device 14 through a small incision of a surgery subject (e.g., a patient) to reach a desired surgical site. Once insertable device 14 is inside the surgery subject via the small incision, the operator may direct movement of insertable device 14 by pushing or pulling on thumb interface 18. For instance, to move the insertable device 14 in a westward direction, the operator may push or pull the west-most portion of thumb interface 18. Insertable device 14 may follow a curved path while being directed westward. As the operator pushes or pulls on thumb interface 18 to have insertable device 14 move westward, camera 16 may enable the operator to view areas near the small incision via external unit 212. The speed of displacement of insertable device 14 may be controlled by the amount of pressure the operator places onto thumb interface 18. External unit 212 may also be used by the operator to manipulate insertable device 14.

Aspects of insertion tool 2 may be single use and may be disposable. Second housing 6, second jacket 10, articulating portion 12, and insertable device 14 may be a single, disposable unit. That is, following use in a laparoscopic procedure, second housing 6, second jacket 10, articulating portion 12, and insertable device 14 may be de-coupled from first jacket 8 and disposed. Optionally, all aspects of insertion tool 2 shown in FIG. 1 may be a single, disposable unit, wherein only third jacket 16 may be decoupled from the electrical power source (not shown) following use in a laparoscopic procedure. The disposability of insertion tool 2 would ensure sterility and enable parts of insertion tool 2 to be made of disposable, yet durable, material. Disposability of insertion tool 2 would also prevent the need for extensive, post-surgical sanitation procedures, as insertion tool 2 would merely be disposed safely (e.g., through medically acceptable biohazardous and medical waste procedures/standards).

Insertable device 14 may be designed to not separate from or decouple with articulating segments 12. This would prevent insertable device 14 from detaching from insertion tool 2 during surgery, and thereby prevent risks to a surgery patient caused by a foreign object being inadvertently placed within their surgery site. This would also prevent difficulties on surgeons operating insertion tool 2, as an inadvertently detached item inside a patient's body would require the surgeons to retrieve the detached item to prevent health complications that could stem from the detached object (e.g., infections, muscle irritation, etc.).

General

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. An insertion tool for inserting devices during a laparoscopic procedure, the tool comprising:

a first housing comprising a joystick module and a circuit board, wherein the joystick module comprises a thumb interface and is coupled to a joystick platform, and the circuit board is positioned closer to the joystick platform relative to the thumb interface;

a second housing comprising a front end and a back end, wherein the second housing comprises a first pulley and a second pulley, the first pulley comprising a first line tension adjustment screw set, and the second pulley comprising a second line tension adjustment screw set, wherein the first pulley is positioned closer to the front end relative to the second pulley;

an insertable device, wherein the insertable device comprises a plurality of sockets;

a first jacket coupled to the first housing and the second housing, wherein the first jacket houses one or more cables configured to transport signals from the joystick module to the second housing; and a second jacket coupled to the second housing and an articulating portion, wherein the second jacket houses a plurality of lines, and wherein the articulating portion comprises articulating segments each comprising a plurality of apertures, the plurality of lines each passing through one of the plurality apertures towards the second housing, via the second jacket, to enable controllable displacement of the articulating segments, wherein one of the plurality of lines is coupled to the first pulley, and another of the plurality of lines is coupled to the second pulley, and the plurality of lines have a ball-shaped end that is coupled to one of the plurality of sockets of the insertable device, thereby coupling the articulating portion to the insertable device.

2. The insertion tool of claim 1, wherein each of the articulating segments comprise a concave side and a convex side.

3. The insertion tool of claim 2, wherein the plurality of apertures comprises a first aperture, a second aperture, a third aperture, a fourth aperture, and a fifth aperture, wherein the first, second, third, and fourth apertures are positioned substantially 90 degrees away from one another, and the fifth aperture is located in between the first, second, third, and fourth apertures and is larger than the first, second, third, and fourth apertures.

4. The insertion tool of claim 2, wherein the articulating segments are arranged so that the concave side of each articulating segment is in contact with the concave side of another articulating segment, while the convex side of each articulating segment is in contact with the convex side of another articulating segment.

5. The insertion tool of claim 1, wherein the first pulley further comprises a first arm and a second arm coupled to the first line tension adjustment screw set, and the second pulley further comprises a third arm and a fourth arm coupled to the second line tension adjustment screw set.

6. The insertion tool of claim 1, wherein the first pulley comprises a first rotation plane and the second pulley comprises a second rotation plane, and the first rotation plane and the second rotation plane are substantially perpendicular to each other.

7. The insertion tool of claim 6, wherein the first pulley and the first rotation plane displace the plurality of lines in a substantially vertical direction, and the second pulley and the second rotation plane displace the plurality of lines in a substantially horizontal direction.

8. The insertion tool of claim 1, wherein the second housing comprises a first motor and a second motor, wherein the first motor is coupled to a first worm gear, and the second motor is coupled to a second worm gear.

9. The insertion tool of claim 8, wherein the first worm gear is coupled to the first pulley, and the second worm gear is coupled to the second pulley.

10. The insertion tool of claim 9, wherein the joystick module is configured to displace the first motor and the second motor.

11. The insertion tool of claim 1, wherein the second jacket further comprises a tube, the tube comprising a plurality of notches, wherein the plurality of notches is configured to restrict movement of the plurality of lines and to prevent the plurality of lines from contacting one another.

12. The insertion tool of claim 1, wherein the second jacket further comprises pathways, wherein each pathway is configured to enclose one of the plurality of lines, and wherein each one of the plurality of pathways aligns with one of the plurality of apertures of the articulating segments.

13. The insertion tool of claim 1, wherein the first housing further comprises a strain relief located closer to the circuit board relative to the joystick module.

14. The insertion tool of claim 1, wherein the articulating segments are configured to displace the insertable device following movement of the plurality of lines, and to maintain the position of the insertable device following displacement.

15. The insertion tool of claim 1, wherein the second housing further comprises a first mounting bracket coupled to the first worm gear, and a second mounting bracket coupled to the second worm gear.

16. The insertion tool of claim 1, wherein the insertable device further comprises:

a flexible housing;

a camera;

a sensor;

at least two LED lights;

a lens flush located above the camera;

a motor for moving the camera in relation to the flexible housing with pan and tilt capabilities, wherein the camera maintains the same horizon regardless of the camera position.

17. The insertion tool of claim 16, wherein the insertable device further comprises cords, wherein the cords exit a back of the insertable device, the cords providing signal and image information to an external unit.

* * * * *